(12) United States Patent
Bryant, Jr. et al.

(10) Patent No.: US 11,035,767 B1
(45) Date of Patent: Jun. 15, 2021

(54) APPARATUS FOR DETERMINING SWOLLEN-POLYMER CROSS-LINK DENSITY

(71) Applicant: The United States of America As Represented by the Secretary of the Navy, Indian Head, MD (US)

(72) Inventors: William F. Bryant, Jr., Temple Hills, MD (US); John N. Kelley, Owings Mills, MD (US)

(73) Assignee: The United States of Americas as represented by the Secretary of the Navy, Washington, DC (US)

(*) Notice: Subject to any disclaimer, the term of this patent is extended or adjusted under 35 U.S.C. 154(b) by 266 days.

(21) Appl. No.: 16/501,561

(22) Filed: May 1, 2019

(51) Int. Cl.
*G01N 3/16* (2006.01)

(52) U.S. Cl.
CPC ..... *G01N 3/165* (2013.01); *G01N 2203/0092* (2013.01); *G01N 2203/0236* (2013.01)

(58) Field of Classification Search
CPC ............. G01N 3/08; G01N 3/16; G01N 3/165
See application file for complete search history.

(56) References Cited

U.S. PATENT DOCUMENTS

| | | | |
|---|---|---|---|
| 5,095,757 A * | 3/1992 | Larsen | G01N 3/04 73/857 |
| 9,157,877 B2 | 10/2015 | Hidalgo et al. | |
| 10,928,281 B2 * | 2/2021 | Iwakiri | G01H 13/00 |
| 2012/0321844 A1 | 12/2012 | Nakahama et al. | |
| 2014/0123773 A1 * | 5/2014 | Lemmer | G01N 3/04 73/863.01 |

FOREIGN PATENT DOCUMENTS

| | | |
|---|---|---|
| JP | 2007240359 | 12/2003 |
| JP | 2003344322 A | 12/2007 |
| JP | 2014081309 A * | 5/2014 |

OTHER PUBLICATIONS

Polymer Testing 45 (pp. 174-178) (Jun. 23, 2015) "Dynamical Mechanical Analysis (DMA) as an Assay of Cross-Link Density of Orthopaedic Ultra High Molecular Weight Polyethylene".

(Continued)

*Primary Examiner* — Erika J Villaluna
(74) *Attorney, Agent, or Firm* — Fredric J. Zimmerman (57) ABSTRACT

An apparatus to determine the swollen cross-link density of a polymeric specimen. The apparatus includes a support structure, a fluid-holding structure to hold a solvent, a first gripping assembly engaged with a weight scale and adapted to grip a specimen and a second gripping assembly adapted to grip the specimen. The fluid-holding structure is attached to a multi-stage device attached to the support structure and displaceable upward or downward. A mechanism supported by the support structure and engaged with the multi-stage device and configured to displace the multi-stage device in fine gradations. When a specimen is gripped by the gripping assemblies and submerged in the solvent and the mechanism displaces the multi-stage device downward, a tensile force is exerted on the specimen. The tensile force is measured by a displacement gauge.

19 Claims, 8 Drawing Sheets

(56) References Cited

OTHER PUBLICATIONS

Journal of Rubber Research, vol. 7(4), 2004 (pp. 248-264) "Determination of the Crosslink Densities of Filled Rubbers by Cyclic Pre-straining".
Report No. RK-TR-70-6 "Crosslink Density Determinations for Polymeric Materials" (Jan. 1970) U.S. Army Missile Command, Redstone Arsenal, Alabama.
Product Literature for "Swell Ratio Tester" made by Cambridge Polymer Group (Jun. 3, 2011).
Swell Ratio Tester Report (Sep. 2004) Indian Head Division, NSWC.
Office of Naval Research, Technical Report No. 6 (Aug. 22, 1990) "Determination of the Crosslink Density of Polymeric Beads by Swelling".

\* cited by examiner

APPARATUS FOR DETERMINING SWOLLEN-POLYMER CROSS-LINK DENSITY

STATEMENT OF GOVERNMENT INTEREST

The invention described herein may be manufactured and used by or for the Government of the United States of America for governmental purposes without the payment of any royalties thereon or therefor.

CROSS REFERENCE TO OTHER PATENT APPLICATIONS

None.

FIELD OF THE INVENTION

The present invention relates to an apparatus for determining swollen-polymer cross-link density.

BACKGROUND

There are many important factors to consider when formulating energetic compositions for chemical propulsion systems. One such factor is "Energy-Density". The Energy-Density refers to the energy packaged within an available envelope and sufficient to perform a mission or role. Another factor, "Energy-Management", is the release of stored energy in a manner required to complete the intended mission or role. Another important factor, "Structure", requires that the energetic composition exhibit structural strength that is adequate to perform the required mission or role. Energetic compositions may include solid propellants, such as slurry-processable, gravity-castable solid propellants. Such solid propellants may be viewed as thermosetting, solid-filled liquid polymers that solidify upon controlled heating into a solid structure of the required shape. A cast solid-propellant charge may be viewed as a composite material or structure. In the terminology of composites, such material comprises three (3) volumes, the sum of which is the volume of the resultant material or structure, $V_t$:

$$V_t = V_f + V_r + V_v, \text{ where}$$

$V_f$=fiber volume;
$V_r$=resin volume (or binder matrix volume), and
$V_v$=void volume.

Analogously, solid-propellant fillers replicate the reinforcing fiber, the binder (and any constituent soluble in the binder) and the resin. The existence or formation of microscopic voids or vacuoles diminishes the strength of the propellant structure. As in the resin of composites, the propellant binder matrix communicates the structural load between the reinforcing solids. Castable solid-propellant compositions, which nominally may comprise 20 to 30 volume-percent binder, might be viewed as dilute. Hence, individual filler-particles may reasonably accommodate each other unlike compacted compositions. This arrangement highlights the structural importance of the binder matrix. Often at issue is the mechanical integrity of composite structures. Unlike the well-understood state of failure in metals, composite structures do not require the achievement of a "two-or-more-pieces" condition in order to exhibit failure. In contrast, the criterion for failure of a composite may be defined as "that state at which the material or structure can no longer perform its intended function".

Therefore, it is critical to determine the integrity of a composite structure prior to formulating and designing a chemical propulsion system using polymers to form such a composite structure. One conventional technique is to measure the polymer/plasticizer interaction parameters in order to determine the integrity of a composite structure. However, the measurement of the polymer/plasticizer interaction parameters is complex and very time consuming. Variability in polymers, such as HTPB Rubber R45M Resins and the resultant mechanical behavior of HTPB-based compositions have necessitated a need for a new and improved analysis-type apparatus that will facilitate a fundamental understanding of the structure-property relationships yielded by large-scale HTPB synthetic practice. Specifically, what is needed is a new apparatus that may accurately and precisely analyze the structural integrity of composite structures such as polymer-based composites. In particular, such a new apparatus must be able to precisely obtain pertinent data for use in determining crosslink-densities in swollen polymers and in filled-polymers wherein the polymers have been decoupled from the fillers via a swelling-solvent.

SUMMARY OF THE INVENTION

It is an aspect of the present invention to provide a novel apparatus to characterize the structural/mechanical behavior of swollen neat and/or filled/extracted thermosetting polymeric materials. The apparatus facilitates determination of the equilibrium modulus of a solvent-swollen polymeric tensile specimen. The determined equilibrium modulus is used to determine the cross-link density of the swollen polymeric tensile specimen at low-levels of damage.

In some exemplary embodiments, the present invention is directed to an apparatus for use in determining swollen polymer cross-link density, including a support structure that includes a plurality of elongate members, a first shelf attached to the plurality of elongate members and a second shelf attached to the plurality of elongate members and positioned below and spaced apart from the first shelf. The first shelf is substantially parallel to the second shelf. Each elongate member includes a lower section that functions as a leg of the support structure. A weight scale is positioned on the first shelf and includes a device to indicate weight (i.e. force) that is applied to the scale. The apparatus further includes a first specimen gripping assembly engaged with the weight scale and configured to grip a specimen to be analyzed. A multi-stage device is slidably attached to the second shelf such that the multi-stage device is displaceable in an upward direction or a downward direction. The multi-stage device includes an upper platform located between the first shelf and the second shelf, a lower platform that is beneath the second shelf and a plurality of vertical guide columns that are slidably disposed through corresponding through-holes in the second shelf and which are attached to the upper platform and the lower platform. The apparatus further includes a mechanism that is supported by the support structure and is engaged with the multi-stage device to displace the multi-stage device in fine gradations. The apparatus further includes a fluid-holding structure having a fluid impermeable structure and a base member upon which the fluid impermeable structure is mounted. The base member has a first portion that cooperates with the impermeable structure to form an interior region for holding fluids. The base member has a second portion that is external to the interior region and is attached to the upper platform of the multi-stage device. The apparatus further includes a second specimen gripping assembly within the interior region of the fluid-holding structure and having a first section attached to the first portion of the base member and a second section that is configured to grip a specimen. When a specimen is gripped by the first specimen gripping assembly and the second specimen gripping assembly and the interior region is filled with fluid, the specimen is submerged in the fluid. A displacement gauge is mounted to the second shelf to measure displacement of the multi-stage device. When the interior region is filled with fluid and a specimen having an initial length is submerged within the fluid and gripped by the first specimen gripping assembly and the second specimen gripping assembly and the mechanism displaces the multi-stage device downward, a tensile force is exerted on the specimen. The tensile force is represented as a weight by the weight scale and the distance traversed by the multi-stage device is measured by the displacement gauge. The distance traversed by the multi-stage device represents an increase in the length of the specimen resulting from the tensile force.

Certain features and advantages of the present invention have been generally described in this summary section. However, additional features, advantages and embodiments are presented herein or will be apparent to one of ordinary skill of the art in view of the drawings, specification and claims hereof. Accordingly, it should be understood that the scope of the invention shall not be limited by the particular exemplary embodiments disclosed in this summary section.

DETAILED DESCRIPTION OF EXEMPLARY EMBODIMENTS OF THE INVENTION

As used herein, the terms "comprises", "comprising", "includes", "including", "has", "having" or any other variation thereof, are intended to cover a non-exclusive inclusion. For example, a process, method, article or apparatus that comprises a list of elements is not necessarily limited to only those elements, but may include other elements not expressly listed or inherent to such process, method, article or apparatus.

It is to be understood that throughout this description, terms such as "vertical", "horizontal", "top", "bottom", "upper", "lower", "middle", "above", "below" and the like are used for convenience in identifying relative locations of various components and surfaces relative to one another in reference to the drawings and that the apparatus of the present invention may be installed and used in substantially any orientation so that these terms are not intended to be limiting in any way.

Approximating language, as used herein throughout the specification and claims, may be applied to modify any quantitative representation that could permissibly vary without resulting in a change in the basic function to which it is related. Accordingly, a value modified by a term such as "about" or "approximately" is not limited to the precise value specified.

As used herein, the term "specimen" shall mean a piece, portion, section or sample of a material that is to be tested and/or analyzed by the apparatus of the present invention.

Figure 1:
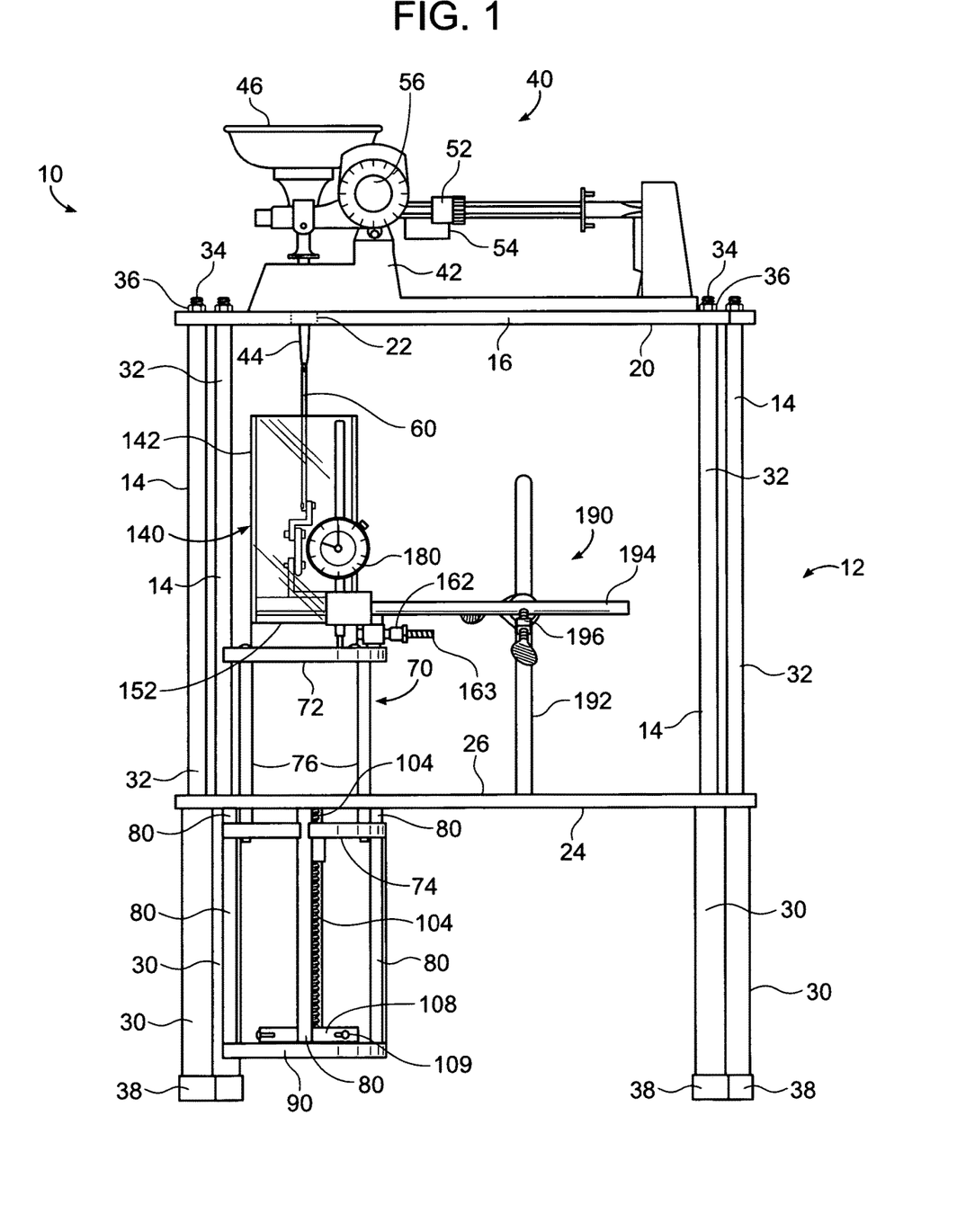
FIG. 1 is a side elevational view of an apparatus for use in determining the cross-link density of a swollen-polymer in accordance with an exemplary embodiment of the present invention.
Figure 2:
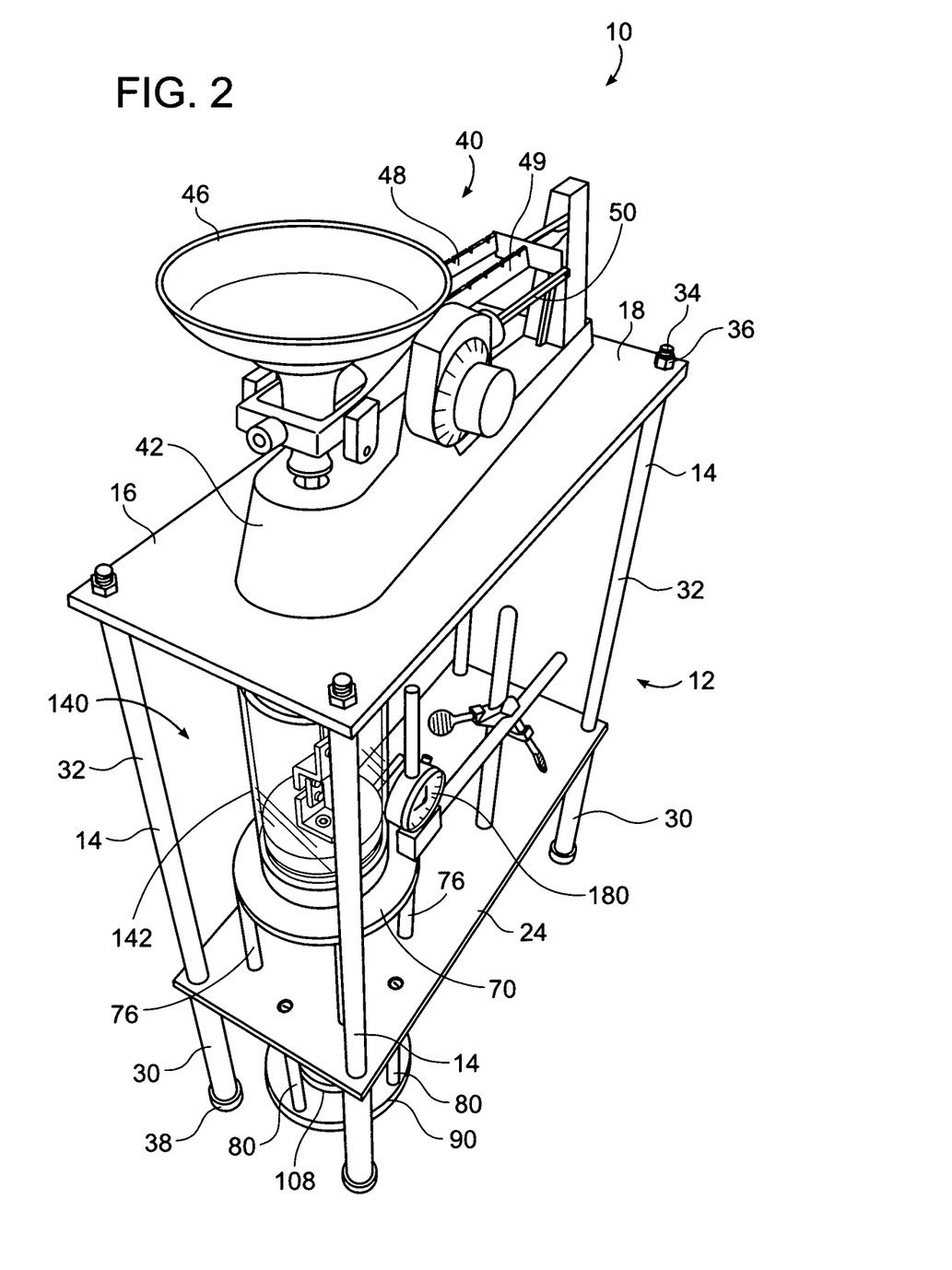
FIG. 2 is a perspective view of the apparatus of FIG. 1.

Referring to FIGS. 1 and 2, there is shown apparatus 10 for determining swollen polymer cross-link density in accordance with an exemplary embodiment of the invention. Apparatus 10 includes support structure 12, which includes a plurality of elongate, vertically oriented support members 14 and top shelf or support member 16 that is attached or secured to support members 14, such that the top shelf 16 is stationary with respect to support members 14. In an exemplary embodiment, top shelf 16 is removably attached to support members 14 by any suitable means. Top shelf 16 includes top side 18 and bottom side 20. Top shelf 16 has through-hole 22, the purpose of which is described in the ensuing description. Top shelf 16 may be fabricated from any one of a variety of rigid or stiff materials, e.g. wood, metal, etc. Support structure 12 further includes bottom shelf or support member 24 that is attached or secured to support members 14 such that bottom shelf 24 is stationary with respect to support members 14. In an exemplary embodiment, bottom shelf 24 is removably attached to support members 14 by any suitable means. Bottom shelf 24 includes top side 26 and bottom side 28 (see FIGS. 4 and 5). Bottom shelf 24 may be fabricated from any one of a variety of stiff or rigid materials (e.g. wood, steel, etc.). Bottom shelf 24 is spaced apart from and substantially parallel to top shelf 16.

Referring to FIGS. 1 and 2, top shelf 16 has through-holes through which portions of vertically oriented support members 14 extend. Each support member 14 has section 30 and section 32. In an exemplary embodiment, section 30 has a circular cross-section and a first diameter and section 32 has a circular cross-section and a second diameter that is less than the first diameter. Each support member 14 has threaded end 34 which has a third diameter that is less than the second diameter of the second section 32. The difference in the second diameter and third diameters creates a shoulder upon which top shelf 16 rests. Threaded ends 34 protrude from the openings in top shelf 16. Nuts 36 are threadedly engaged to the threaded ends 34 to secure top shelf 16 to the support members 14. Referring to FIG. 1, in an exemplary embodiment, bottom shelf 24 has a threaded through-hole (not shown) in each corner and each vertically oriented member 14 has a threaded portion (not shown) that is threadedly engaged with a corresponding threaded through-hole in bottom shelf member 24. However, it is to be understood that other suitable techniques may be used to attach bottom shelf 24 to vertically oriented members 14. In one exemplary embodiment, cap member 38 is attached to the bottom end of each section 30. Cap members 38 are fabricated from hardened steel. Suitable materials also may include rubber, resin, plastic, composite materials, etc. The difference between the first diameter and the second diameter creates a shoulder (not shown) upon which bottom shelf 24 rests.

Referring to FIGS. 1 and 2, scale 40 is positioned on top side 18 of top shelf 16 such that it is located over opening 22 in top shelf 16. Scale 40 measures the weight that is applied thereto. In an exemplary embodiment, scale 40 is a beam balance scale. Scale 40 includes base 42 and tabs (not shown) on the underside of base 42 that are positioned in corresponding detents (not shown) in top side 18 of top shelf 16. Such a configuration prevents movement of scale 40. The underside of base 42 includes an opening (not shown) that provides access to the components within scale 40. Link or wire 44 extends through through-hole 22 in top shelf 16 and into the opening (not shown) in the underside of base 42 and is engaged with the components of scale 40 such that pulling link or wire 44 downward will exert a weight on scale 40.

Scale 40 includes platform 46 and beams 48, 49 and 50 (see FIG. 2). In an exemplary embodiment, scale 40 includes zero to one-hundred gram Poise 52, zero to five-hundred gram Poise 54 and counter-balancing dial 56. The function of dial 56 is to allow for fine weight measurements, e.g. $\frac{1}{10}$ gram. The weight applied to scale 40, either due to a downward force applied to link 44 or an object positioned in platform 46, is the sum of the values of the Poise positions, read directly from the graduated beams, and the position of dial 56. In an exemplary embodiment, scale 40 is a commercially available 2600 Series Balance Scale manufactured by Ohaus Corporation of Florham Park, N.J.

Figure 8:
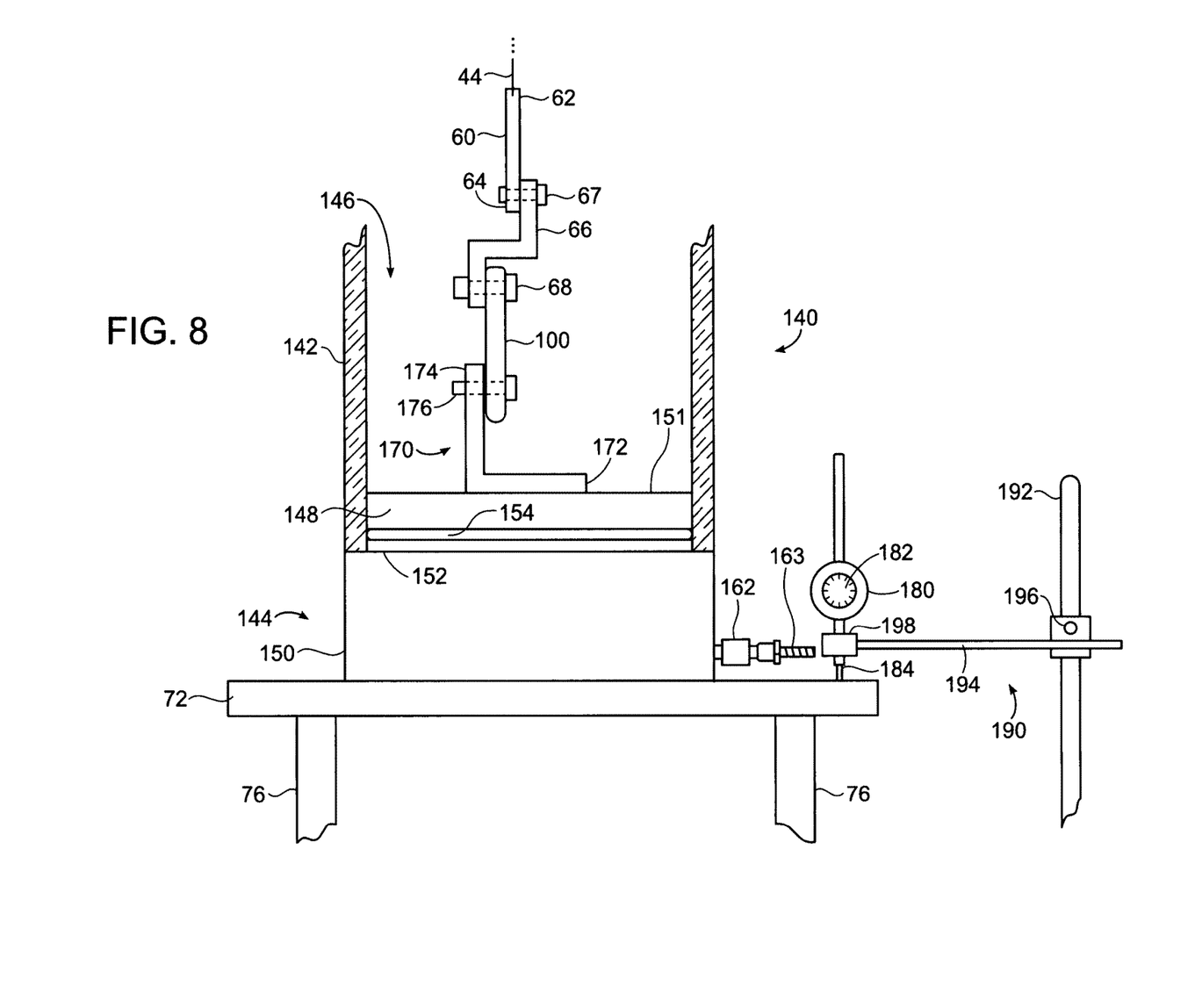
FIG. 8 is a partial view, in elevational and partially in cross-section, of the apparatus of FIG. 1.

Referring to FIGS. 1, 2 and 8, apparatus 10 further includes a first specimen gripping assembly which comprises elongate member 60. In an exemplary embodiment, elongate member 60 includes a flexure member that is fabricated from a flexible strip of metal. In another exemplary embodiment, elongate member 60 comprises a metal rod. In a further exemplary embodiment, elongate member 60 is fabricated from a corrosion-resistant metal such as stainless steel. In another exemplary embodiment, elongate member 60 is fabricated from stainless steel and has a thickness of about 0.015 inch. Elongate member 60 includes first end portion 62 and opposite second end portion 64. First end portion 62 is attached to link or wire 44. As shown in FIG. 8, elongate member 60 is vertically oriented. The first specimen gripping assembly further includes first grip device 66. Opposite second end portion 64 of elongate member 60 is configured or adapted to be removably attached to first grip device 66. First grip device 66 includes fastening device 67. In an exemplary embodiment, opposite end portion 64 of elongate member 60 is removably attached to first fastening device 67. First grip device 66 includes second fastening device 68. Second fastening device 68 is removably attached to one end of specimen 100. In an exemplary embodiment, first grip device 66 is an "ESS-shaped" Aluminum bracket. In an exemplary embodiment, first fastening device 67 and second fastening device 68 are comprised of corrosion-resistant screws or bolts and nuts. Since first end portion 62 of elongate member 60 is attached to link or wire 44, any downward or tensile force applied to elongate member 60 is represented by a weight indicated by scale 40.

Figure 3:
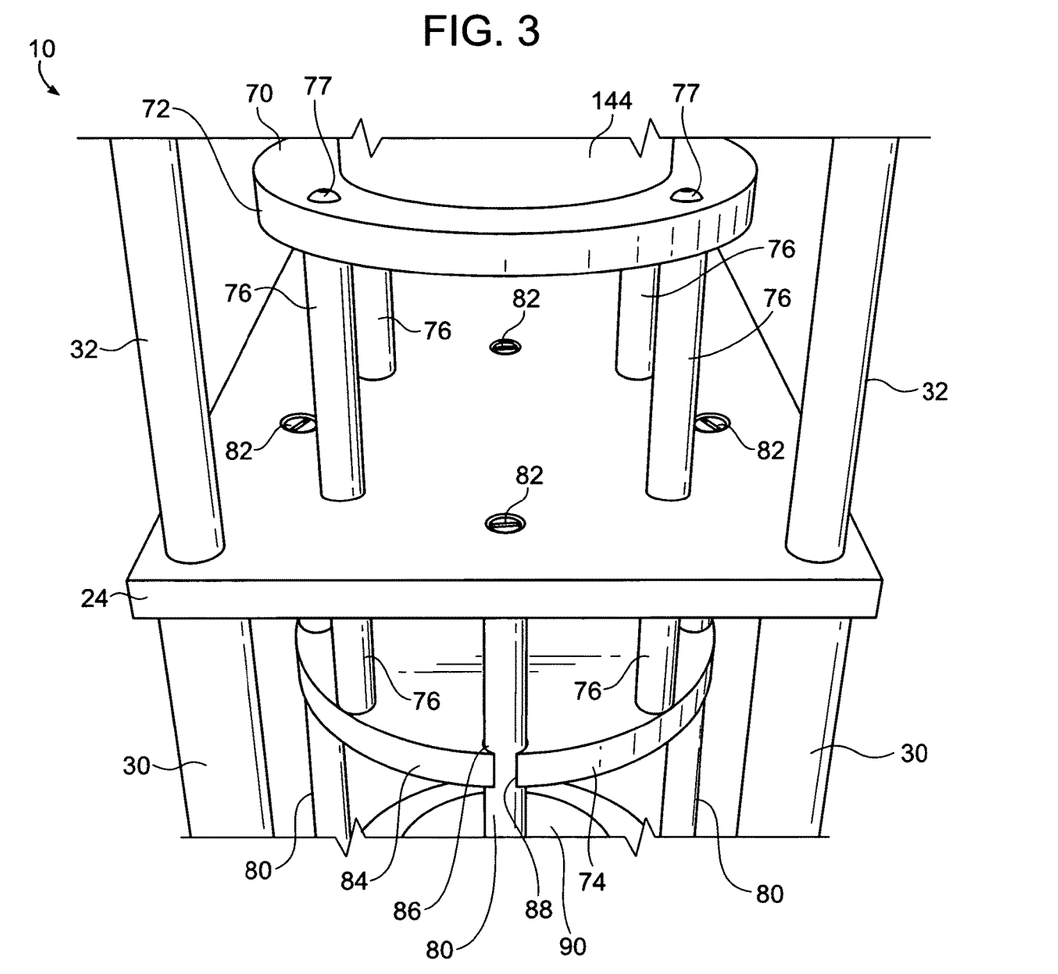
FIG. 3 is a partial view, in perspective, of the apparatus of FIG. 1, the view showing a multi-stage device that is configured for linear movement in either the upward or downward direction.
Figure 4:
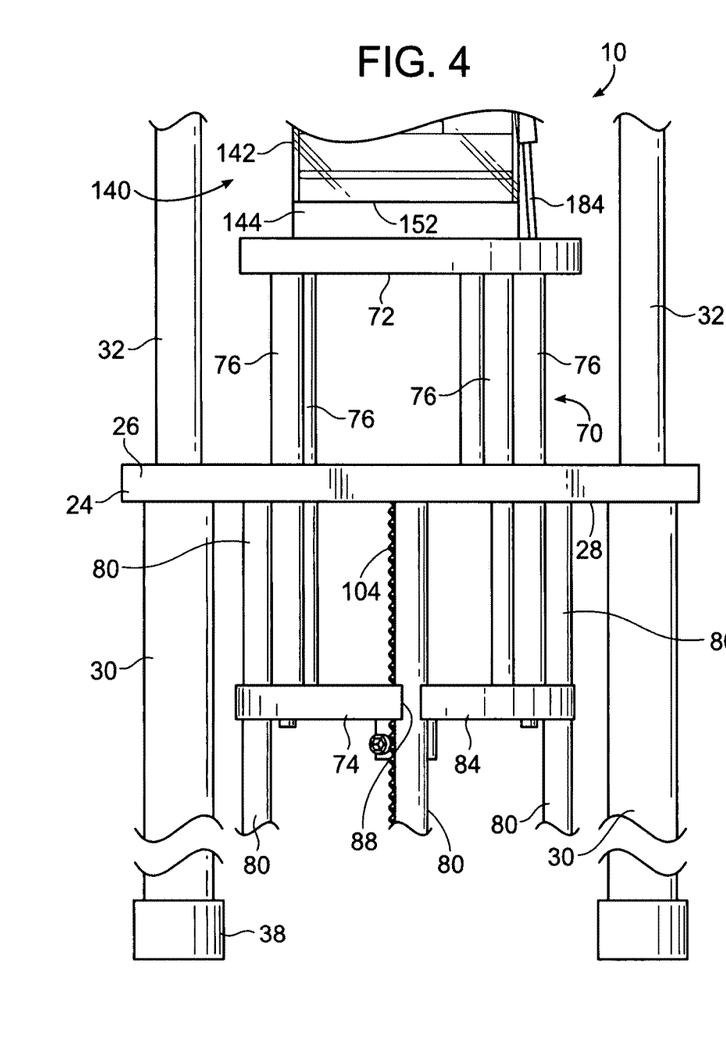
FIG. 4 is a partial view, in elevational, of the apparatus of FIG. 1, the view showing the multi-stage device shown in FIG. 3.
Figure 5:
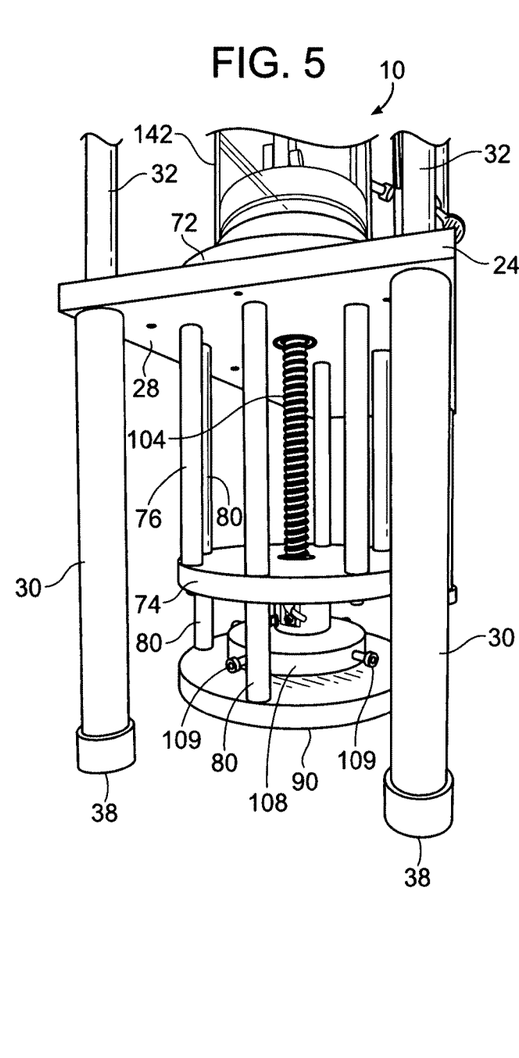
FIG. 5 is a partial view, in perspective, of the apparatus of FIG. 1, the view showing a mechanism that effects linear displacement of the multi-stage device.

Referring to FIGS. 1 and 3-7, apparatus 10 further comprises multi-stage device 70 that is slidably attached to bottom shelf 24. Multi-stage device 70 may slide upward or downward with respect to bottom shelf 24. The movement of multi-stage device 70 is linear. Multi-stage device 70 includes an upper platform 72 located between top shelf 16 and bottom shelf 24, a lower platform 74 that is beneath bottom shelf 24 and a first plurality of guide columns 76 that are slidably disposed through corresponding openings in bottom shelf 24 and which are attached to upper platform 72 and lower platform 74. In an exemplary embodiment, guide columns 76 are attached to upper platform 72 and lower platform 74 via screws or fasteners 77 (see FIGS. 6 and 7). In an exemplary embodiment, upper platform 72 has a substantially circular shape. In an exemplary embodiment, lower platform 74 has a substantially circular shape. Apparatus 10 further includes a plurality of rails 80 that are located beneath and attached to bottom shelf 24 and which extend downward to distal ends. Lower platform 74 is slidably attached to rails 80. In an exemplary embodiment, the upper end of each rail 80 has a threaded bore (not shown) that is aligned with a corresponding opening in bottom shelf 24. As shown in FIG. 3, a corresponding screw or threaded fastener 82 is threadedly engaged with each threaded bore of a corresponding rail 80. In an exemplary embodiment, rails 80 are equidistantly spaced. Referring to FIGS. 3-5, lower platform 74 has perimetrical edge 84 and a plurality of equidistant spaced openings 86 that are in proximity to perimetrical edge 84. Each rail 80 extends through a corresponding opening 86. In an exemplary embodiment, perimetrical edge 84 has a plurality of gaps 88 therein wherein each gap 88 exposes the spatial region that defines each corresponding opening 86.

In such a configuration, each rail member 80 is visible through the corresponding gap 88. Lower platform 74 slides upon rails 80 in a linear motion, either in the upward or downward direction. Rails 80 are sturdy and rigid and therefore, allow for smooth and precise movement of multi-stage device 70. As shown in FIGS. 1, 2 and 5, apparatus 10 includes bottom support plate 90 that is rigidly attached to the distal ends of rails 80. In an exemplary embodiment, bottom support plate 90 is substantially circular in shape. In an exemplary embodiment, upper platform 72, lower platform 74, guide columns 76, rails 80 and bottom support plate 90 are fabricated from metal such as aluminum, steel, stainless steel, nickel, etc.

Referring to FIGS. 1 and 4-7, apparatus 10 further comprises a mechanical linear actuator to linearly displace multi-stage device 70 upward or downward in fine gradations. In one embodiment, the mechanism comprises a commercially available ball-screw assembly which is well known in the mechanical field. The mechanical linear actuator includes upper ball-bearing assembly 102 that is connected to bottom shelf 24. In one embodiment, upper ball-bearing assembly 102 is partially embedded within bottom shelf 24. The mechanical linear actuator further includes a lower ball-bearing assembly (not shown) that is similarly connected to bottom support plate 90. The mechanical linear actuator further includes threaded shaft 104 which defines helical raceway 105 configured for ball bearings. Threaded shaft 104 has a first end rotatably engaged with upper ball-bearing assembly 102. Threaded shaft 104 extends through a central opening (not shown) in rotatable member 108 which is described in detail in the ensuing description. Threaded shaft 104 has an opposite second end that is rotatably engaged with the lower ball-bearing assembly (not shown) that is connected or anchored to bottom support plate 90. In an exemplary embodiment, the lower ball-bearing assembly is anchored in a central counter-bore in bottom support plate 90. The mechanical linear actuator further includes recirculating ball-nut 106 that is mounted to threaded shaft 104. Recirculating ball-nut 106 includes ball bearings (not shown) therein that are configured to fit within helical raceway 105 of threaded shaft 104. Recirculating ball-nut 106 is attached to lower platform 74 of multi-stage device 70 (see FIG. 6). The mechanical linear actuator further includes rotatable member 108 that is attached to threaded shaft 104. In an exemplary embodiment, separate threaded fasteners (not shown) join rotatable member 108 to threaded shaft 104. Rotation of rotatable member 108 causes rotation of threaded shaft 104. Members 109 radially extend from rotatable member 108 and function as aids that allow a user or operator to rotate rotatable member 108 in fine increments in order to precisely lower multi-stage device 70 in fine gradations.

Rotatable member 108 is positioned in proximity to bottom support plate 90. Spacer 110 provides a space or gap between bottom support plate 90 and rotatable member 108. Rotatable member 108 functions as a hand wheel and can be easily rotated by a user of apparatus 10. Rotation of rotatable member 108 in a first direction 111 (e.g. clockwise) causes recirculating ball-nut 106 to traverse helical raceway 105 of threaded shaft 104 in an upward direction thereby displacing multi-stage device 70 upward. Rotation of rotatable member 108 in an opposite second direction 112 (e.g. counterclockwise) causes recirculating ball-nut 106 to traverse helical raceway 105 in a downward direction that displaces multi-stage device 70 downward.

Referring to FIGS. 1, 2, 8 and 9, apparatus 10 further includes fluid-holding structure 140. Fluid-holding structure 140 includes fluid impermeable structure 142 and base member 144 that cooperate to form interior region 146 for holding fluids, e.g. solvents, water, etc. Impermeable structure 142 is fabricated from a material that does not allow fluids to pass therethrough. In an exemplary embodiment, impermeable structure 142 comprises a cylindrical member. In one embodiment, the cylindrical member comprises a glass cylinder that provides a clear view of the interior region 146 and the fluids therein. In an exemplary embodiment, the glass cylinder is fabricated from borosilicate. Impermeable structure 142 is removably attached or mounted to base member 144. Base member 144 includes first portion 148 within interior region 146 and second portion 150 that is external to interior region 146. Base member 144 is attached to upper platform 72 of multi-stage device 70. In an exemplary embodiment, base member 144 is rigidly attached to upper platform 72 via centrally located screws or bolts (not shown). However, other suitable techniques and fasteners may be used to attach base member 144 to upper platform 72. First portion 148 includes top surface 151.

Second portion 150 is attached to upper platform 72. First portion 148 of base member 144 has a first diameter and second portion 150 has a second diameter that is greater than the first diameter, wherein the difference between the first diameter and second diameter creates shoulder 152. Impermeable structure 142 sits upon shoulder 152. First portion 148 functions as a plug or closure for impermeable structure 142. In an exemplary embodiment, first portion 148 has a diameter of about 3.50 inches and a height of about 1.00 inch and second portion 150 has a height of about 2.00 inches and a diameter of about 4.00 inches. Base member 144 includes seal 154 that creates a fluid-tight seal between cylindrical member 142 and first portion 148. In an exemplary embodiment, seal 154 comprises an "O" ring seal. In such an embodiment, seal 154 is sized to fit around first portion 148 and fit in a circumferentially extending grove or channel (not shown) that is adjacent to or contiguous with shoulder 152.

Figure 9:
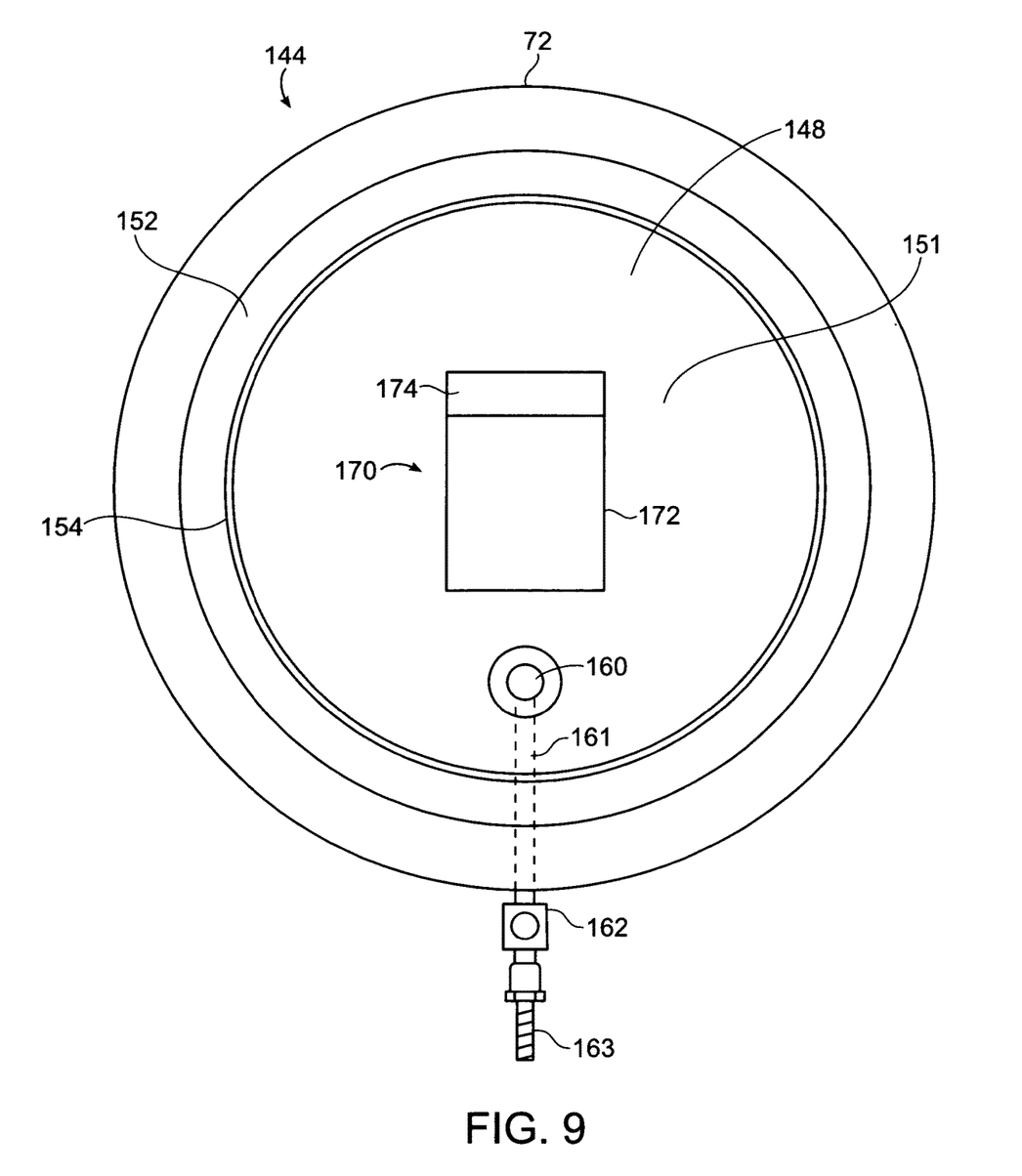
FIG. 9 is a plan view of the base member and second specimen gripping assembly.

Referring to FIG. 9, base member 144 includes an opening 160 that allows fluids to drain from interior region 146 and also allows fluids to enter interior region 146. Opening 160 is in fluid communication with an internal channel or fluid conduit 161 (shown in phantom) that is within base member 144. This internal channel or fluid conduit 161 is in fluid communication with fluid valve 162 that is attached or mounted to second portion 150. When the fluid valve 162 is opened, the fluid in interior region 146 flows into opening 160, through internal channel 161 and out through fluid valve 162. Fluid valve 162 includes hose barbs 163 and is also configured to be connected to a source of fluid and therefore can be used to fill interior region 146 with a fluid such as a solvent. Fluid valve 162 allows fluid to drain from or flow into interior region 146 without exposing the users to the fluids which, in some instances, may be toxic. In an exemplary embodiment, base member 144 is fabricated from nylon.

As shown in FIGS. 8 and 9, second grip device 170 is located within interior region 146 and includes first section 172 that is attached to first portion 148 of base member 144. Any suitable fastening technique may be used to attach first section 172 to first portion 148. In exemplary embodiments, screws, bolts, rivets or similar fasteners are used to attach first section 172 to first portion 148. In one embodiment, a centrally located screw (not shown) is used to attach first section 172 to first portion 148. In an exemplary embodiment, first section 172 is centrally located upon top surface 151. Second grip device 170 further includes second section 174. In an exemplary embodiment, second section 174 is substantially perpendicular to first section 172. Second section 174 includes fastening device 176 that is configured to be removably attached or fastened to specimen 100. In an exemplary embodiment, second grip device 170 comprises a commercially available "ELL" aluminum bracket. In an exemplary embodiment, fastening device 176 comprises a corrosion-resistant screw or bolt and complementary nut.

Referring to FIGS. 1, 2 and 8, apparatus 10 further comprises displacement gauge 180 which measures the linear movement of multi-stage device 70. Displacement gauge 180 includes dial face 182 that indicates displacement in a particular unit of measure. Displacement gauge 180 further includes calibrated stem 184. Dial face 182 indicates the distance in which calibrated stem 184 moves. Dial face 182 is configured to measure linear movement in graduations. For example, if dial face 182 is configured to measure displacement in inches, the graduations are 0.0010 inch. In an exemplary embodiment, displacement gauge 180 is a commercially available Mitutoyo A.D.G. Dial Indicator 2424-10 or equivalent. The distal end of calibrated stem 184 contacts the upper platform 72 of multi-stage device 70. Linear movement of multi-stage device 70, either upward or downward, is translated to a displacement which is indicated on dial face 182. As shown in FIG. 1, apparatus 10 further includes displacement gauge holder device 190. Holder device 190 includes vertical member 192 which has one end attached to bottom shelf 24. Any suitable method may be used to attach vertical member 192 to bottom shelf 24. In an exemplary embodiment, vertical member 192 is removably attached to bottom shelf 24. In one embodiment, the distal end of vertical member 192 has a threaded end which engages a corresponding threaded-hole (not shown) in bottom shelf 24 and threadedly engaged with it. Holder device 190 further includes horizontal member 194 that is movably attached to vertical member 192 via clamp assembly 196. Horizontal member 194 is attached to junction box 198. Clamp assembly 196 allows adjustment of horizontal member 194 so that calibrated stem 184 of displacement gauge 180 can be correctly positioned on upper platform 72.

Figure 6:
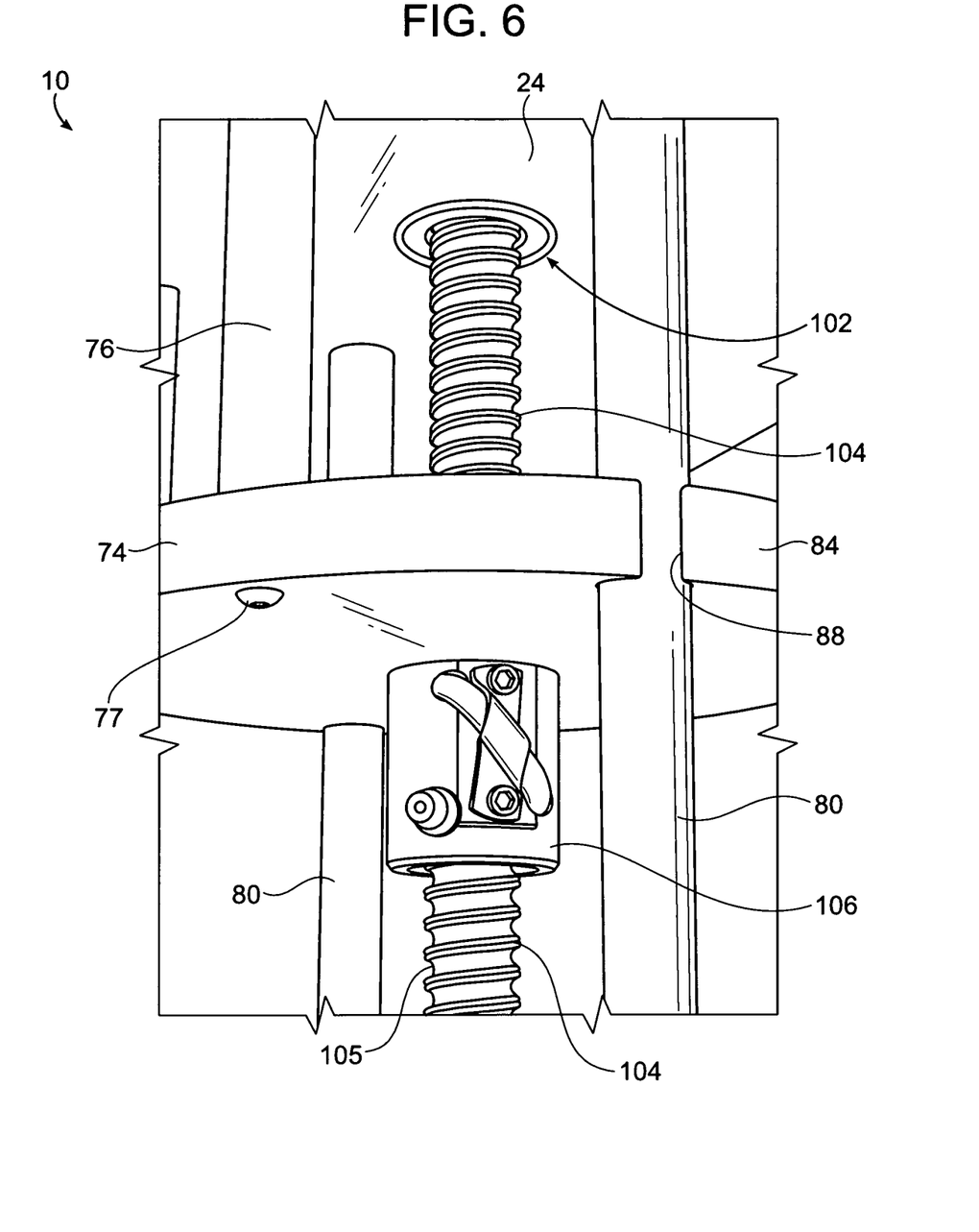
FIG. 6 is a partial view, in perspective, of the mechanism shown in FIG. 5.
Figure 7:
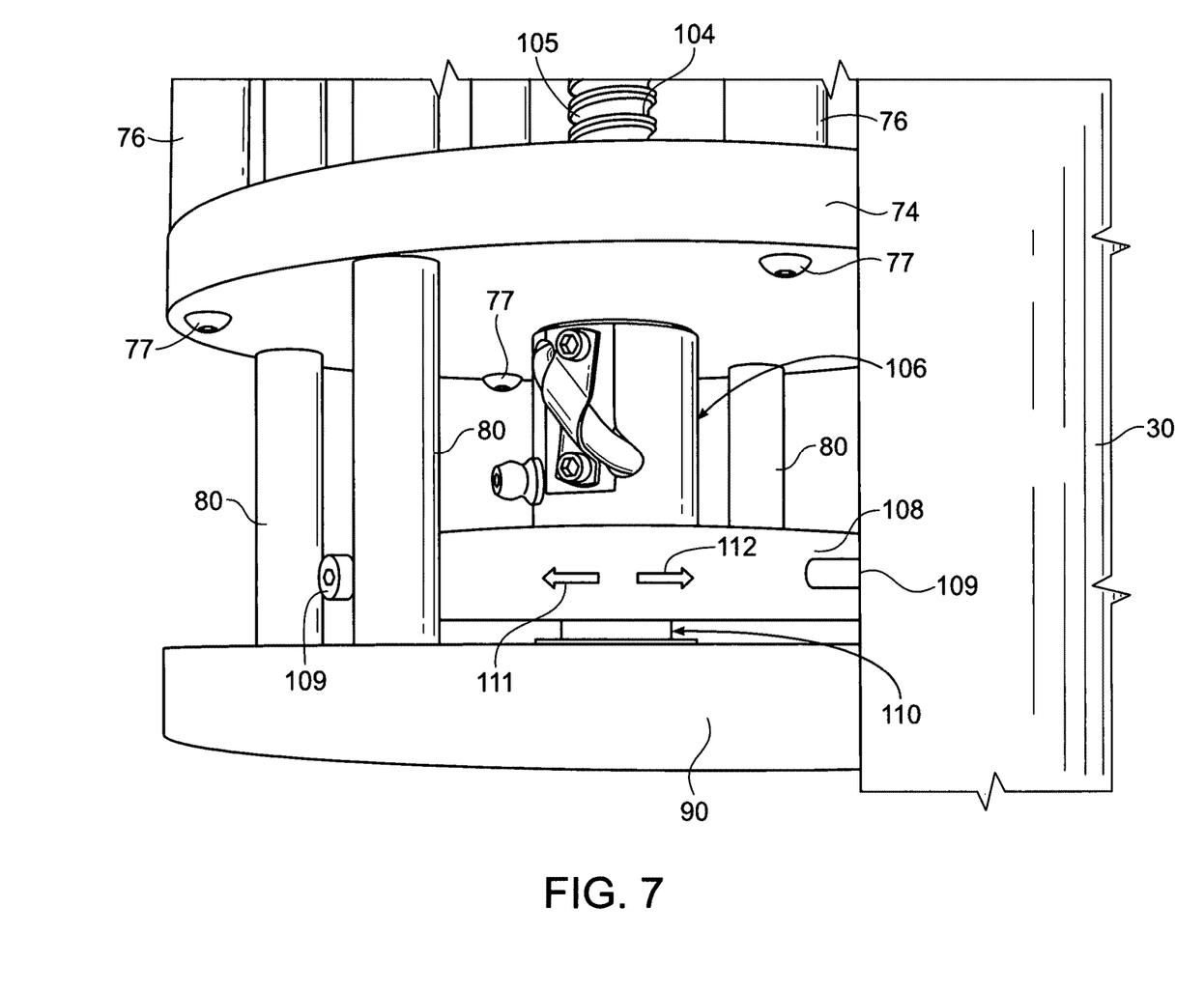
FIG. 7 is an enlargement of a portion of the view shown in FIG. 5, the view showing components of the mechanism that effect linear displacement of the multi-stage device.

In order to determine the cross-link density of a swollen polymer, a polymer specimen 100 is attached to second fastening device 68 of first grip device 66 and fastening device 176 of second grip device 170 as shown in FIG. 8. Fluid valve 162 is then connected to a fluid source and interior region 146 of fluid-holding structure 140 is filled with a fluid. Typically, the fluid is a solvent having predetermined properties and characteristics. Also typically, polymer specimen 100 is pre-solvent-swollen prior to attachment. Polymer specimens typically swell from about 2.8 inches in length to about 3.8 inches in length, or about 36%. Next, scale 40 is zeroed out using dial 56 and Poise 52 and/or Poise 54, as appropriate. The position of displacement gauge 180 is adjusted so that calibrated stem 184 contacts upper platform 72 of multi-stage device 70, and shown in FIGS. 1, 3 and 4. Referring to FIGS. 5-7, in order to exert a tensile force upon polymer specimen 100, a user rotates rotatable member 108 in counter-clockwise direction 112 so as to cause recirculating ball-nut 106 to traverse helical raceway 105 of threaded shaft 104 in a downward direction. Such movement of recirculating ball-nut 106 results in multi-section device 70 moving downward. Due to the configuration of the mechanical linear actuator, the downward movement of multi-stage device 70 is in relatively small gradations. As a result of the downward movement of multi-stage device 70, a tensile force is exerted on both ends of polymer specimen 100. As described in the ensuing description, one end of polymer specimen 100 is attached to first grip device 66. First grip device 66 is attached to flexure member 60. Flexure member 60 is attached to link or wire 44 which is engaged with weight scale 40 as shown in FIGS. 1 and 2. Therefore, the tensile force exerted on polymer specimen 100 is represented by a weight indicated by weight scale 40. Displacement gauge 180 measures the downward displacement of multi-stage device 70. The measured displacement represents the increase in the length of polymer specimen 100 due to stretching caused by the tensile force. As the user rotates rotatable member 108 in the counterclockwise direction, the displacement of multi-stage device 70 increases, as indicated by displacement gauge 180, and the tensile force exerted on polymer specimen 100 increases. The increase in tensile force results in greater weight being exerted on scale 40. As a result, there is a specific measured weight for each measured displacement. Each measured weight, expressed as a tensile force, is determined by bringing the scale to "null" after each recorded increase in displacement and recording the tensile force required to "null" the scale at that displacement. Thus, apparatus 10 allows several measurements of the Force-Displacement (F-X) behavior of the swollen-polymer network within the defined swollen polymer specimen 100. The measured Force-Displacement data are used to determine the equilibrium Young's Modulus of the swollen polymer specimen 100. The swollen-polymer modulus is then used to determine the crosslink-density of the swollen-polymer specimen 100.

Apparatus 10 provides many benefits and advantages. For example, a borosilicate cylinder 142 provides a clear view of interior region 146. It is relatively easy to attach polymer specimen 100 to first grip device 66 and second grip device 170. The first grip device 66 and the second grip device 170 are fabricated from materials that will not corrode or deteriorate due to exposure to the solvent. Base member 144 includes drain 160 and fluid drain valve 162 which allow interior region 146 to be completely drained of solvent while minimizing user exposure to the solvent. Guide columns 76 and rigid rails 80 cooperate with the mechanical linear actuator to provide precise, smooth, linear movement of multi-stage device 70 thereby substantially eliminating jitter, shaking and hysteresis. Rotatable member 108 allows a user of apparatus 10 to easily lower multi-stage device 70 in relatively small gradations. Thus, strain is precisely and smoothly applied to the oval, cured polymer specimen 100 in desired increments. This allows very accurate Force-Displacement data to be obtained. The configuration of displacement gauge 180 and its position relative to multi-stage device 70 improves repeatability of displacement data.

The reinforcement generally provided by the solids in cured, filled specimens (e.g. composite solid propellants and PBX's) is decoupled from the binder matrix. Thus, apparatus 10 may be used to study the behavior of the binder matrix in both new and aged materials.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

Finally, any numerical parameters set forth in the specification and attached claims are approximations (for example, by using the term "about") that may vary depending upon the desired properties sought to be obtained by the present invention. At the very least, and not as an attempt to limit the application of the doctrine of equivalents to the scope of the claims, each numerical parameter should at least be construed in light of the number of significant digits and by applying ordinary rounding.

What is claimed is:

1. An apparatus for use in determining swollen polymer cross-link density, comprising:
    a support structure including a plurality of elongate members, a first shelf being attached to the plurality of elongate members and a second shelf being attached to the plurality of elongate members and positioned below and spaced apart from the first shelf, wherein each elongate member includes a section that functions as a leg of the support structure;
    a weight scale being positioned on the first shelf and including a device to indicate force applied to the scale;
    a first specimen gripping assembly being engaged with the weight scale and configured to grip a specimen;
    a multi-stage device being slidably attached to the second shelf such that the multi-stage device is displaceable in an upward direction or a downward direction, the multi-stage device including an upper platform located between the first shelf and the second shelf, a lower platform being situated beneath the second shelf and a plurality of vertical guide columns being slidably disposed through corresponding through-holes in the second shelf and which are attached to the upper platform and the lower platform;
    a mechanism being supported by the support structure and engaged with the multi-stage device to displace the multi-stage device in fine gradations;
    a fluid-holding structure including a fluid impermeable structure and a base member upon which the fluid impermeable structure is mounted, the base member includes a first portion to cooperate with the impermeable structure to form an interior region to hold fluids and a second portion, which is external to the interior region and is attached to the upper platform of the multi-stage device;

a second specimen gripping assembly comprising a first section being attached to the first portion of the base member and a second section being configured to grip a specimen; and a displacement gauge being mounted to the support structure for measuring displacement of the multi-stage device, wherein the interior region of the fluid-holding structure contains a fluid therein, wherein a specimen, which includes an initial length, is submerged within the fluid and attached to the first specimen gripping assembly and the second specimen gripping assembly, wherein the mechanism is operated to displace the multi-stage device downward where a tensile force is exerted on the specimen, wherein the tensile force is represented as a weight by the weight scale and the distance traversed by the multi-stage device is measured by the displacement gauge, and wherein said distance represents an increase in the length of the specimen caused by the tensile force.

2. The apparatus according to claim 1, wherein the fluid impermeable structure of the fluid-holding device comprises a substantially cylindrical member fitted over the first portion of the base member.

3. The apparatus according to claim 2, wherein the cylindrical member is a glass cylindrical member.

4. The apparatus according to claim 2, wherein the first portion of the base member includes a first diameter, wherein the second portion of the base member includes a second diameter greater than the first diameter, and wherein a difference between the first diameter and second diameter creates a shoulder upon which the cylindrical member is seated.

5. The apparatus according to claim 1, wherein the fluid-holding device includes a seal on the base member to form a fluid-tight seal between the base member and a walled structure.

6. The apparatus according to claim 1, wherein the first shelf is substantially parallel to the second shelf.

7. The apparatus according to claim 1, wherein the base member includes a fluid port to allow fluids to flow one of out of and into the interior region of the fluid-holding structure.

8. The apparatus according to claim 7, further comprising a fluid valve attached to the second portion of the base member and in fluid communication with the fluid port.

9. The apparatus according to claim 1, wherein the mechanism further comprises a mechanical linear actuator.

10. The apparatus according to claim 9, wherein the mechanical linear actuator comprises a ball-screw assembly.

11. The apparatus according to claim 1, further comprising:

a plurality of rails being attached to and extending down from the second shelf, wherein the lower platform of the multi-stage device is slidably attached to the plurality of rails; and a bottom support member being attached to the plurality of rails and being positioned beneath the second shelf.

12. The apparatus according to claim 11, wherein the mechanism comprises a mechanical linear actuator which includes:

an upper ball-bearing assembly connected to the second shelf;

a lower ball-bearing assembly connected to the bottom support member;

a threaded shaft defines a helical raceway and a first end rotatably engaged with the upper ball-bearing assembly and a second end rotatably engaged with the lower ball-bearing assembly;

a recirculating ball-nut mounted to the threaded shaft and includes ball bearings configured to move within the helical raceway, the recirculating ball-nut is attached to the lower platform of the multi-stage device; and said mechanism further comprises a rotatable member attached to the threaded shaft and in proximity to the bottom support member, the rotatable member is rotatable in a first direction that causes the recirculating ball-nut to upwardly traverse the threaded shaft thereby displacing the multi-stage device upward and rotatable in an opposite second direction that causes the recirculating ball-nut to downwardly traverse the threaded shaft thereby displacing the multi-stage device downward.

13. The apparatus according to claim 1, wherein the first shelf includes a through-hole therein and the weight scale is positioned over the through-hole, and wherein the first specimen gripping assembly comprises:

a flexure member includes a first end portion and an opposite second end portion;

a link member attached to the flexure member and extended through the through-hole and engaged with the weight scale; and a first grip device attached to the opposite second end portion of the flexure member and adapted to be removably attached to a specimen.

14. The apparatus according to claim 13, wherein the flexure member is a corrosion-resistant metal flexure member.

15. The apparatus according to claim 1, further comprising a displacement gauge holder structure being attached to the support structure for steadily holding the displacement gauge at a desired position with respect to the multi-stage device.

16. The apparatus according to claim 15, wherein the displacement gauge holder structure is adjustable to allow adjustment of the position of the displacement gauge.

17. The apparatus according to claim 1, wherein the upper platform of the multi-stage device is substantially circular in shape.

18. The apparatus according to claim 1, wherein the lower platform of the multi-stage device is substantially circular in shape.

19. The apparatus according to claim 1, wherein the scale comprises a multi-beam scale.

* * * * *